(12) United States Patent
Wahl

(10) Patent No.: US 11,389,222 B2
(45) Date of Patent: Jul. 19, 2022

(54) MEDICAL PIN REMOVAL TOOL

(71) Applicant: DEPUY SYNTHES PRODUCTS, INC., Raynham, MA (US)

(72) Inventor: Michael Wahl, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 255 days.

(21) Appl. No.: 16/793,725

(22) Filed: Feb. 18, 2020

(65) Prior Publication Data

US 2021/0251676 A1    Aug. 19, 2021

(51) Int. Cl.
*A61B 17/88* (2006.01)
*A61B 17/86* (2006.01)

(52) U.S. Cl.
CPC ........ *A61B 17/8886* (2013.01); *A61B 17/861* (2013.01)

(58) Field of Classification Search
CPC . A61B 17/162; A61B 17/861; A61B 17/8872; A61B 17/8886; A61B 17/8891; B25B 13/5066
See application file for complete search history.

(56) References Cited

U.S. PATENT DOCUMENTS

| 2,024,852 A | 12/1935 | Gagne |
| 2,287,069 A | 6/1942 | Stone et al. |
| 2,613,942 A * | 10/1952 | Saunders .............. B25B 23/103 279/72 |
| 2,985,049 A | 5/1961 | Vilmerding |
| 3,889,557 A | 6/1975 | Young |

(Continued)

FOREIGN PATENT DOCUMENTS

| DE | 3644442 C1 | 6/1988 |
| DE | 4301582 A1 | 7/1993 |

(Continued)

OTHER PUBLICATIONS

Written Opinion re PCT/IB2021/050630; dated May 6, 2020; 8 pgs.
(Continued)

*Primary Examiner* — Samuel S Hanna
(74) *Attorney, Agent, or Firm* — Kramer & Amado, P.C.

(57) ABSTRACT

A cylindrical shaft may be gripped with an apparatus including a housing having an axis and an inner surface with multiple asymmetric cam surfaces, a proximal end including a means to rotate the housing, and a distal end having an opening configured to receive the cylindrical shaft, at least two cylindrical gripping members configured to grip the cylindrical shaft, where each cylindrical gripping member contacts a corresponding asymmetric cam surface at a first rest position, and a rotatable frame which holds each pair of cylindrical gripping members at a fixed angular orientation relative to each other. The rotatable frame is configured to rotate upon insertion of the cylindrical shaft into a space defined by the gripping members so that each gripping member moves away from the axis of the housing along a first portion of the corresponding asymmetric cam surface. After insertion of the cylindrical shaft, the housing is configured to rotate so as to cause each gripping member to move toward the axis of the housing along the corresponding asymmetric cam surface.

13 Claims, 11 Drawing Sheets

(56) References Cited

U.S. PATENT DOCUMENTS

| | | | | |
|---|---|---|---|---|
| 3,908,487 | A * | 9/1975 | Plaw | B25B 15/04 |
| | | | | 81/59.1 |
| 4,724,730 | A | 2/1988 | Mader et al. | |
| 5,315,902 | A | 5/1994 | Ragland et al. | |
| 5,406,866 | A * | 4/1995 | Badiali | B25B 15/02 |
| | | | | 81/57.3 |
| 5,893,851 | A * | 4/1999 | Umber | B23B 31/1071 |
| | | | | 606/80 |
| 6,033,405 | A * | 3/2000 | Winslow | A61F 2/4601 |
| | | | | 606/86 R |
| 6,073,520 | A | 6/2000 | Bueno et al. | |
| 8,997,608 | B2 | 4/2015 | Merrick | |
| 2011/0233949 | A1 * | 9/2011 | Petit | B25B 13/5066 |
| | | | | 294/102.1 |

FOREIGN PATENT DOCUMENTS

| | | |
|---|---|---|
| EP | 0458145 A1 | 11/1991 |
| GB | 2067115 A | 7/1981 |

OTHER PUBLICATIONS

International Searching Authority Search Report re: PCT/IB2021/050630; dated May 6, 2020; 6 pgs.
Translation of EP 0458145 dated Nov. 27, 1991 to Rothenberger Werkzeugemaschinen GmbH.
Translation of DE 3644442 dated Jun. 9, 1988 to Wera Werk Hermann Werner GmbH and Co.
Translation of DE 4301582 dated Jul. 22, 1993 to Koken Tool Co.

* cited by examiner

MEDICAL PIN REMOVAL TOOL

TECHNICAL FIELD

Various embodiments disclosed herein relate generally to an apparatus for gripping and removing a cylindrical shaft. The cylindrical shaft may be, for example, a drill bit or a surgical pin.

BACKGROUND

When bones are broken or damaged, external fixation of the bones with Schantz pins may be required. Such pins may have a threaded distal end which may be screwed into a bone, and a proximal end with flat edge surfaces which may be used to grip the pin during insertion.

When surgeons use Schanz pins with ring fixator systems, the Schanz pins are often cut to make the frames more comfortable for the patients. This has the unfortunate consequence of removing the flats on the Schanz pins that can aid in removal after treatment. One method to remove a Schanz pin is with a three-jaw T-handle chuck. Such three-jaw chucks are able to grip a pin or screw having a smooth shaft, but the surgeon typically cannot tighten the handle sufficiently, allowing the wrench to slip under the removal torque.

SUMMARY

In view of the difficulties with removing surgical pins and screws, including Schanz pins, there is a present need for tools for removing such pins. A brief summary of various exemplary embodiments of such tools is presented herein. Some simplifications and omissions may be made in the following summary, which is intended to highlight and introduce some aspects of the various exemplary embodiments, but not to limit the scope of the invention. Detailed descriptions of a preferred exemplary embodiment adequate to allow those of ordinary skill in the art to make and use the inventive concepts will follow in later sections.

Various embodiments disclosed herein relate to an apparatus for gripping a cylindrical shaft, including:
- a housing having an axis and an inner surface with multiple asymmetric cam surfaces, a proximal end comprising a means to rotate the housing, and a distal end having an opening configured to receive the cylindrical shaft,
- at least two cylindrical gripping members configured to grip the cylindrical shaft, where each cylindrical gripping member contacts a corresponding asymmetric cam surface at a first rest position; and
- a rotatable frame which holds each pair of cylindrical gripping members at a fixed angular orientation relative to each other.

In various embodiments, the rotatable frame is configured to rotate within a cylindrical opening in a distal end of the inner surface of the housing. Upon insertion of the cylindrical shaft into a space defined by the gripping members, each gripping member moves radially away from the axis of the housing along a first portion of the corresponding asymmetric cam surface. After insertion of the cylindrical shaft, the housing is configured to rotate so as to cause each gripping member to move toward the axis of the housing along the first portion of the corresponding asymmetric cam surface, thereby gripping the cylindrical shaft. A torsion spring within the rotatable frame has an end which may engage a lobe in the cylindrical opening in the housing so as to bias the rotatable frame into a first position where each cylindrical gripping member contacts the corresponding asymmetric cam surface at the first rest position. Rotation of the rotatable frame relative to the housing disengages the torsion spring from the lobe in the housing.

In various embodiments, each cylindrical gripping member may independently be a spherical gripping member, a right cylindrical gripping member having planar ends, or a cylindrical gripping member having non-planar ends. Thus, for example, a cylindrical gripping member may be used in combination with cylindrical gripping members, with the various gripping members being angularly spaced from each other.

In various embodiments, each cylindrical gripping member has a first gripping member and a second gripping member, where the second gripping member is coaxial with the first gripping member. Each first gripping member and each second gripping member may be independently selected from the group consisting of a spherical gripping member, a right cylindrical gripping member having planar ends, and a cylindrical gripping member having non-planar ends. Each first gripping member may be a spherical gripping member, and each second gripping member may be a cylindrical gripping member having planar or non-planar ends. A cylindrical gripping member having non-planar ends may have frustoconical ends, dome shaped ends, or a combination thereof.

In various embodiments, the cylindrical gripping members are configured to grip a cylindrical shaft. Each cylindrical gripping member is made of a material which is harder than the cylindrical shaft, where the material may be silicon nitride, zirconium oxide, silicon carbide, or stainless steel.

The housing has an axis and an inner surface with multiple asymmetric cam surfaces, each pair of adjacent asymmetric cam surfaces being connected by a substantially planar surface. A first portion of each asymmetric cam surface has a first curvature, and a second portion of each asymmetric cam surface has a second curvature which is greater than the first curvature.

A proximal end of the housing has a means to rotate the housing, which may be a handle. Alternatively, the means to rotate the housing is a semi-cylindrical shaft configured to engage a handle with a semi-cylindrical bore, the semi-cylindrical shaft having a planar surface and a round surface with a groove therein, the groove being configured to engage a ball bearing mounted in the semi-cylindrical bore. The means to rotate the housing may also be a hexagonal shaft configured to engage a handle with a hexagonal bore, the hexagonal shaft having a groove therein, the groove being configured to engage a ball bearing mounted in the hexagonal bore.

In various embodiments, the current disclosure is directed to a method for removing a cylindrical shaft from a material using an apparatus for gripping a cylindrical shaft as disclosed herein. The method includes:
- inserting a cylindrical shaft into an opening at the distal end of a housing having multiple asymmetric cam surface and multiple cylindrical gripping members, where each cylindrical gripping member contacts a corresponding asymmetric cam surface at a first rest position;
- pushing the cylindrical shaft into a space defined by the cylindrical gripping members so as to cause each gripping member to move away from the axis of the housing along a first portion of the corresponding asymmetric cam surface, thereby expanding the space defined by the cylindrical gripping members until it accepts the cylindrical shaft; and, after insertion of the cylindrical shaft, rotating the housing relative to the rotatable frame so as to cause each gripping member to move toward the axis of the housing along the corresponding asymmetric cam surface until the cylindrical shaft is gripped and deformed by the gripping members; and removing the deformed shaft from the from the material.

Various embodiments disclosed herein relate to an apparatus for gripping a cylindrical shaft, including a housing having an axis and an inner surface with multiple asymmetric cam surfaces, and a distal end having an opening configured to receive the cylindrical shaft; a first rotatable frame within the housing; and a second rotatable frame within the housing. At least two first cylindrical gripping members are held by the first rotatable frame, so that each first cylindrical gripping member contacts a first end of a corresponding asymmetric cam surface. At least two second cylindrical gripping members are held by the second rotatable frame, where each second cylindrical gripping member contacts a second end of the corresponding asymmetric cam surface, opposite to the first end. The first and second cylindrical gripping members are each configured to grip the cylindrical shaft.

In various embodiments, the first and second rotatable frames are configured to rotate in opposite directions upon insertion of the cylindrical shaft into a space defined by the first and second gripping members, so that the first and second gripping members each rotate toward a center of the corresponding asymmetric cam surface. After insertion of the cylindrical shaft, the housing is configured to:

rotate in a first direction so as to cause the first gripping members to move toward the second end of the corresponding asymmetric cam surface, gripping the cylindrical shaft and rotating the cylindrical shaft in the first direction; or rotate in a second direction so as to cause the second gripping members to move toward the first end of the corresponding asymmetric cam surface, gripping the cylindrical shaft and rotating the cylindrical shaft in the second direction.

BRIEF DESCRIPTION OF THE DRAWINGS

In order to better understand various exemplary embodiments, reference is made to the accompanying drawings, wherein.

DETAILED DESCRIPTION

Figure 1:
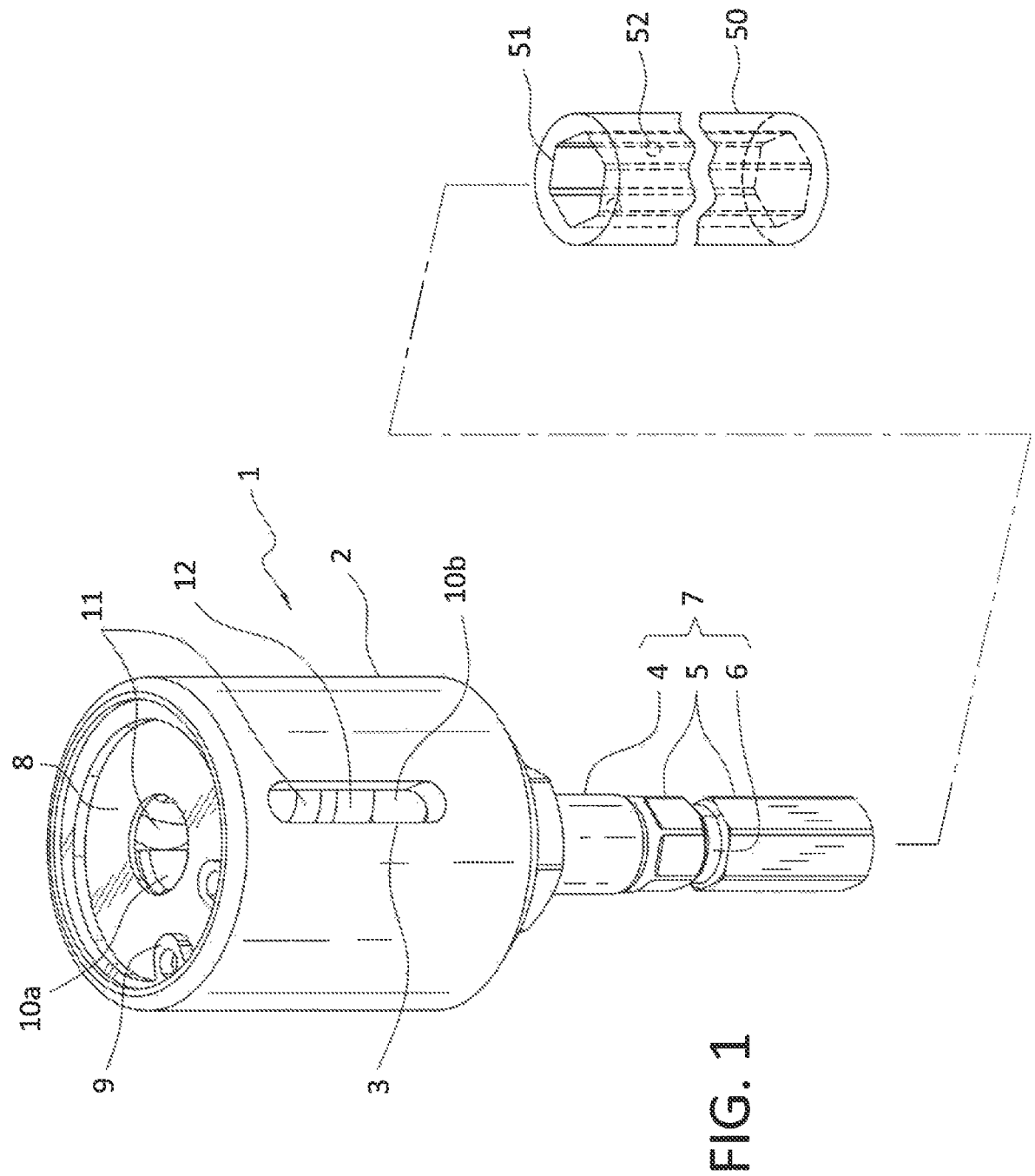
FIG. 1 illustrates a first embodiment of an apparatus for gripping a cylindrical shaft.

Referring now to the drawings, in which like numerals refer to like components or steps, there are disclosed broad aspects of various exemplary embodiments.

Unless otherwise specified, application of the term "cylindrical" to an item in this disclosure means that the item is symmetric, and has at least one axis of rotation.

A first view of an apparatus 1 for gripping a cylindrical shaft, e.g., a surgical pin is shown in FIG. 1, although more detailed views are discussed below. The apparatus includes a cylindrical housing 2, with a rotating means 7 configured to rotate the housing 2 at a proximal end and a washer 8 at a distal end. In various embodiments, the rotating means 7 configured to rotate the housing 2 includes a cylindrical shaft 4 connected to a hexagonal shaft 5, where the hexagonal shaft may have a tapered end. The hexagonal shaft 5 may have a groove 6. The hexagonal shaft is configured to fit into a hexagonal bore 50 of a handle 51. Retractable bearings 52 may be mounted in the handle 50, where the retractable bearings 52 are configured to engage the groove 6 on hexagonal shaft 5, preventing shaft 5 from withdrawing from bore 51.

The housing 2 has a cylindrical shell with optional windows 3 therethrough, which may facilitate cleaning of the apparatus 1. The distal end of housing 2 includes a washer 8 held in place by a clip 9. A spacer 10 within housing 2 has a proximal ring 10b, visible through window 3, and a plurality of spacer arms 10a, one of which is visible through washer 8. The spacer arms extend from ring 10b in a distal direction, toward washer 8. A cylindrical gripping member is positioned between each pair of adjacent spacer arms 10a. Each cylindrical gripping member may be a single member with an axis of symmetry, or multiple members arranged so that they are coaxial and have a common axis of symmetry. In FIG. 1, each cylindrical gripping member features a first spherical member 11 between two arms 10a near washer 8, and a second cylindrical member 12 adjacent to spacer ring 10b.

Figure 2:
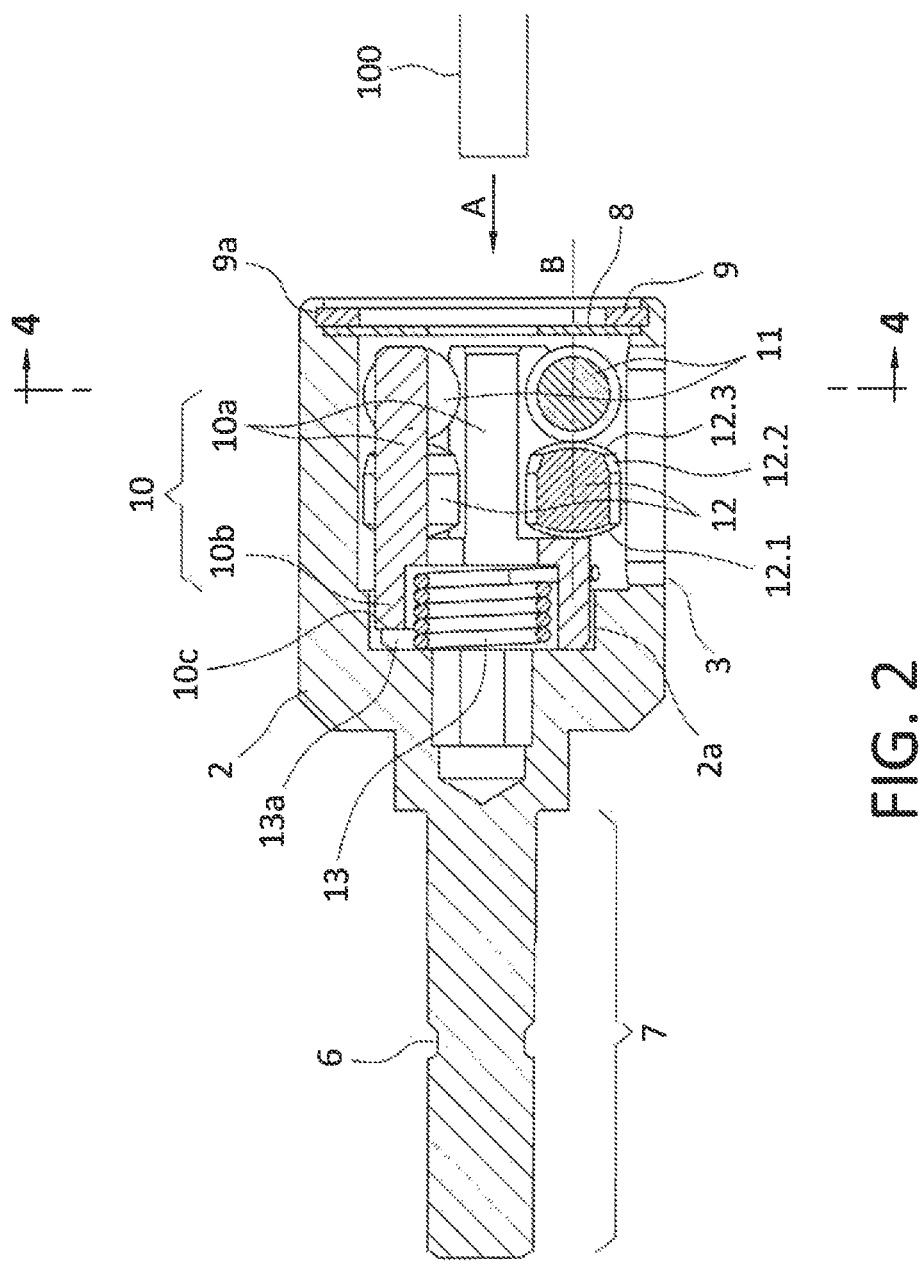
FIG. 2 shows a cross section of the apparatus of FIG. 1.
Figure 3A:
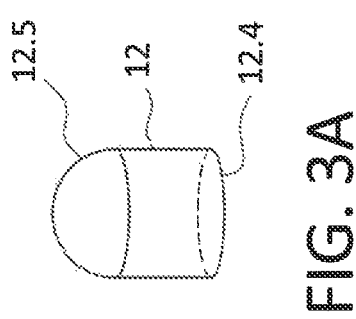
FIGS. 3A and 3B shows exemplary cylindrical gripping members for use in the apparatus of FIG. 1.
Figure 3B:
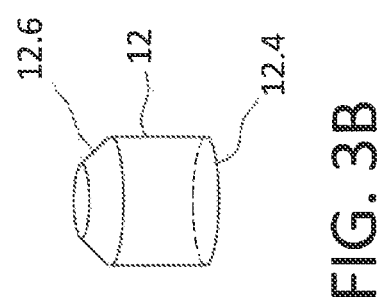

FIG. 2 shows a cross section of the apparatus of FIG. 1. As shown in FIG. 2, spacer 10 has a spacer ring 10b, which fits in a cylindrical opening 2a in the distal end of the interior of housing 2. Within spacer ring 10b, there is a torsion spring 13, which has a free end 13a which extends through an opening 10c in spacer ring 10b. Between each adjacent set of two spacer arms 10a, there is at least one cylindrical gripping member, which may be made of a single member having cylindrical symmetry. Alternatively, multiple cylindrical gripping members, each having an axis of symmetry which is parallel to an axis of housing 2, may be positioned between each adjacent set of two spacer arms 10a. As shown in FIG. 2, each cylindrical gripping member may include a spherical member 11 in combination with a cylindrical member 12, where the spherical member 11 and the cylindrical member 12 have a common diameter and may be generally coaxial with an axis B. Each cylindrical member 12 may have at least one planar end, at least one dome-shaped end 12.1, at least one end with a tapered surface 12.2, or a tapered surface 12.2 in combination with a dome-shaped outer end 12.3. As shown in FIG. 3A, a cylindrical member 12 may have a planar end 12.4 and a hemispherical end 12.5. As shown in FIG. 3B, a cylindrical member 12 may have a planar end 12.4 and a frustoconical end 12.6.

In various embodiments, each gripping member may be formed of a single cylindrical member 12. Alternatively, each gripping member may be formed of two or more spherical members 11. The gripping members are retained in position by arms 10a on each side and washer 8 at the distal end of the housing 2. Washer 8 is retained in position by clip 9, which fits into a circumferential slot on an inner surface of housing 2. The gripping members define a space which is configured to receive a cylindrical shaft 100, which may be inserted through the opening in washer 8.

In various embodiments of the method for removing a cylindrical shaft, the cylindrical shaft is a surgical pin, and the material in which the shaft is positioned is bone. The surgical pin may be a Schanz pin, a Schanz screw, or a Steinman pin. The surgical pin or screw may be used for external fixation. In some cases, the surgical pin may be a pin or screw initially formed with gripping surfaces, e.g., flat surfaces, at an end configured to receive a driving tool. However, the portion of the pin with the gripping surfaces may have been removed after insertion in an external fixation device to allow for increased patient comfort.

Figure 4:
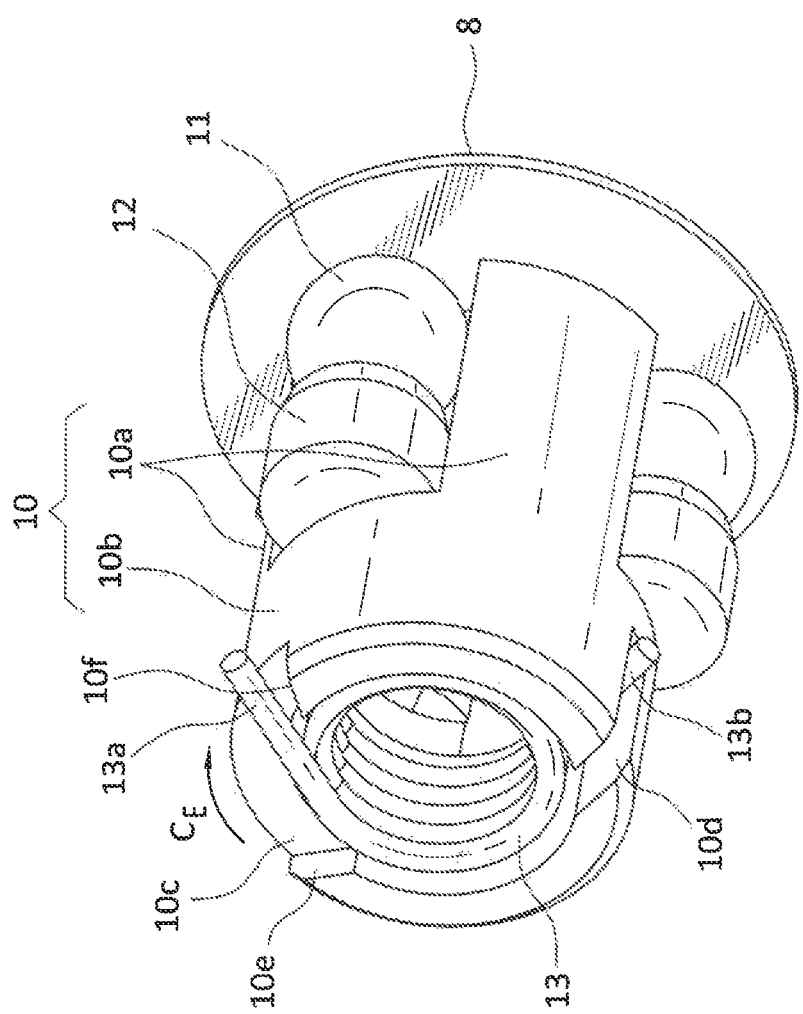
FIG. 4 shows a view of the assembly holding cylindrical gripping members for holding a cylindrical shaft with the apparatus of FIG. 1.

FIG. 4 shows an assembly including spacer 10, a set of cylindrical gripping members, each formed from a spherical gripping member 11 and a cylindrical gripping member 12, washer 8, and torsion spring 13. As seen in FIG. 4, end 13b of spring 13 fits in slot 10d of spacer 10, preventing movement of spring end 13b relative to spacer 10. End 13a of torsion spring 13 normally rests in notch 10c in spacer 10. In the absence of tension on the spring, end 13a rests against wall 10e of notch 10c. Spring end 13a may be rotated about an axis of spacer 10 until spring end 13a contacts wall 10f of notch 10c, thereby applying tension to spring 13.

Figure 5:
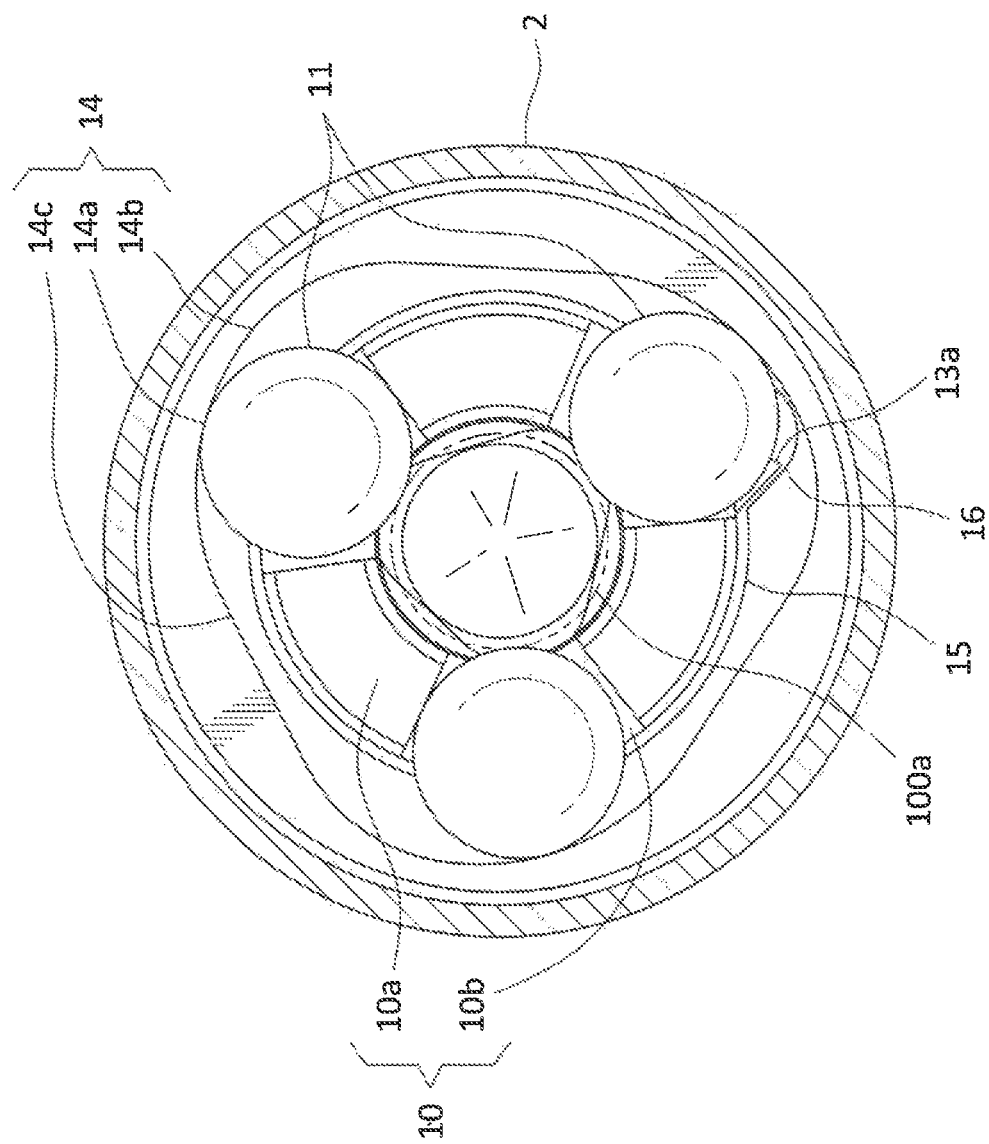
FIG. 5 shows a cross section view of the apparatus of FIG. 1, in the plane holding arrows 4 in FIG. 2.

FIG. 5 is a view of the apparatus of FIG. 2, along the plane of arrows 4. Housing 2 has an inner surface 14 with multiple lobes with a variable radius of curvature, each lobe providing an asymmetric curved cam surface. Each asymmetric cam surface includes a first surface 14a with a larger radius of curvature, e.g., a shallow curvature, and a second surface 14b with a smaller radius of curvature, e.g., a steeper curvature. The asymmetric cam surfaces are connected by a surface 14c, which may be planar, or may have a slight curvature. Surface 14c may curve inwards toward an axis of housing 2. Surface 14c may also curve outwards, away from the axis of housing 2, with the proviso that the outward curvature of surface 14c must be less than the curvature of either surface 14a or 14b. Spacer 10 is positioned in housing 2, with the spacer ring 10b occupying a cylindrical opening 15 at the base of the interior of housing 2. A cylindrical gripping member, shown in FIG. 4 as a spherical member 12, is positioned between each pair of arms 10a on spacer member 10. At rest, each gripping member 11 rests against a first surface 14a of an asymmetric cam surface on inner surface 14 of housing 2. The gripping member 11 define a space 100a which is configured to receive cylindrical shaft 100 as shown in FIG. 2. When each gripping member 11 rests against a first surface 14a of an asymmetric cam surface, space 100a is generally too small to receive shaft 100.

Figure 6:
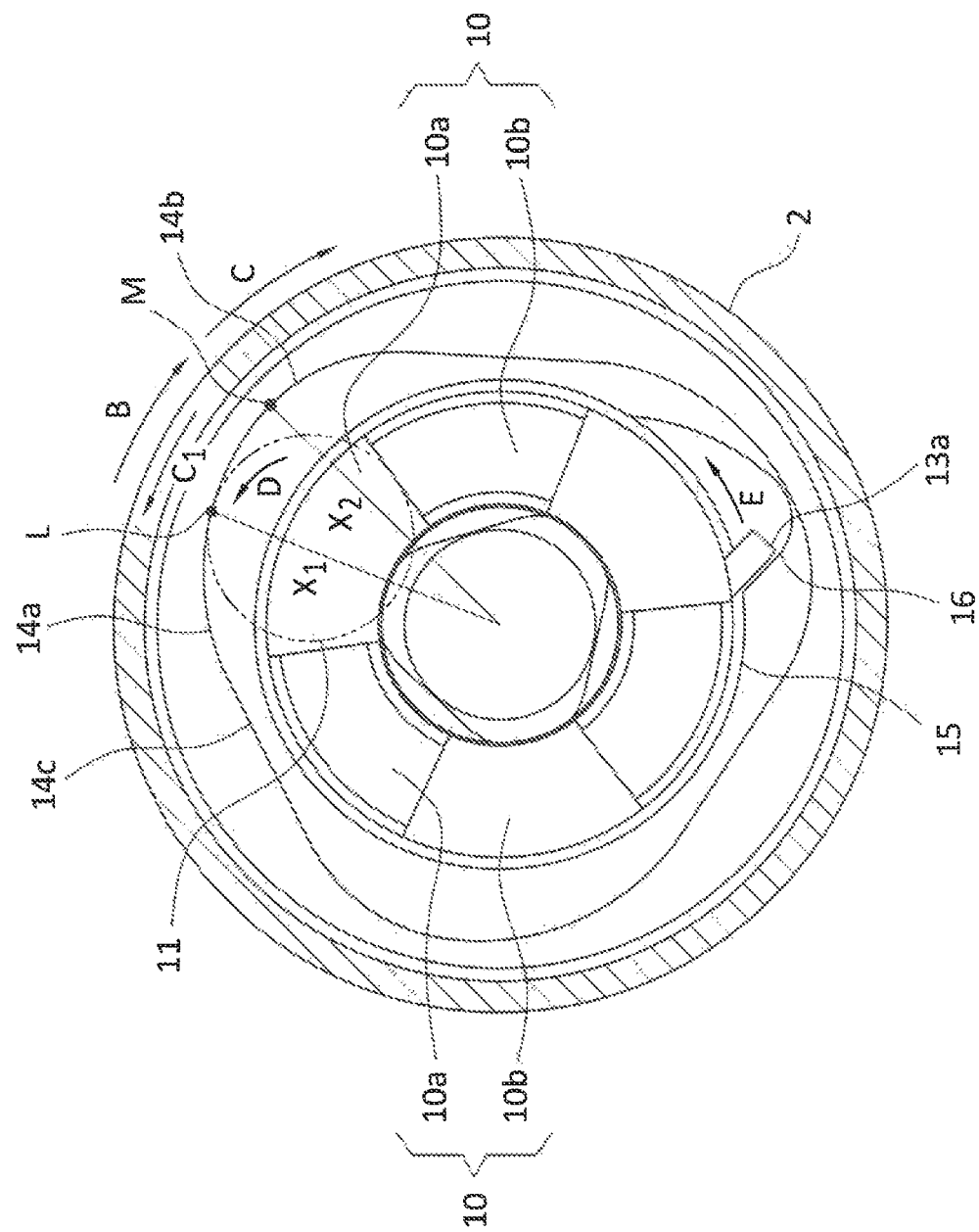
FIG. 6 shows a cross section view of the apparatus of FIG. 1, illustrating movement of cylindrical gripping elements relative to the inner cam surface of the housing.

As seen in FIG. 6, a gripping member 11 (shown as a dotted circle for purposes of clarity) initially rests against cam surface 14a at point L. Since the space 100a defined by members 11 (shown in FIG. 4) is too small to receive cylindrical shaft 100, as shown in FIG. 2, shaft 100 cannot be inserted into housing 2 while each gripping member rests at point L, where the distance from the axis of housing 2 to point L is $x_1$. However, upon insertion of shaft 100 along the axis of housing 2, gripping members 11 are free to revolve in the direction of arrow D relative to the inner surface of housing 2, allowing spacer 10 and gripping members 11 to move in the direction of arrow B in the direction of point M, which is the boundary between first surface 14a of the asymmetric cam surface and second surface 14b of the asymmetric cam surface. Rotation of the gripping member 11 in the direction of arrow B may continue until gripping member 11 rests against the inner surface of housing 2 at or near point M. When each gripping member 11 rests at point M, the distance from the axis of housing 2 to point M is $x_2$, where $x_2 > x_1$ and is sufficiently large to allow cylindrical shaft 100 to enter space 100a defined by members 11 and be gripped by gripping members 11. In some embodiments where the sum of the radius of shaft 100 and the diameter of gripping member 11 is $x_2$, the gripping member 11 may come to rest at point M upon insertion of shaft 100. If the sum of the radius of shaft 100 and the diameter of gripping member 11 is between $x_1$ and $x_2$, the gripping member 11 may come to rest between points L and M upon insertion of shaft 100.

As shown in FIG. 6, the free end 13a of spring 13 (only 13a shown in FIG. 5) is pressed against a surface of a lobe 16 in cylindrical opening 15 occupied by spacer 12. Rotation of spacer 10 relative to housing 2 is prevented prior to insertion of a cylindrical shaft 100 by the wall of lobe 16, with spacer 10 being biased into a position where gripping members 11 each rest against an inner surface of housing 2 at a point L. As shaft 100 is inserted and spacer 10 rotates in the direction of arrow B, the tension on torsion spring 13 increases, with the free end 13a of torsion spring moving in the direction of arrow E out of lobe 16 as the spacer 10 rotates relative to lobe 16.

After insertion of cylindrical shaft 100, shaft 100 is tightly gripped by members 11. Rotation of housing 2 in the direction of arrow C causes gripping members 11 to move toward point L along the first surface 14a of the asymmetric cam surface, opposite to arrow B. As the gripping members move in the direction of point L, the gripping members tighten on shaft 100, compressing the shaft. Rotation of housing 2 may proceed until each gripping member 11 returns to point L, or until the gripping members tighten on shaft 100 so that further rotation is not possible. Once each gripping member 11 rests at point L, or between points L and M, the space 100a defined by members 11 is significantly smaller than the diameter of cylindrical shaft 100. Thus, when each gripping member 11 rests at or near point L, the gripping members compress the cylindrical shaft 100.

After each gripping member 11 rests at or near point L, further rotation of housing 2 in the direction of arrow C tightens the grip of gripping members 11 on the cylindrical shaft 100, and also allows for rotation of cylindrical shaft 100. Rotation of housing 2 in a direction opposite to arrow C loosens the grip of gripping members 11 on the cylindrical shaft 100, allowing withdrawal of the cylindrical member 100. Alternate rotation of housing 2 allows for a ratcheting motion, involving:

a) rotation of the housing 2 and shaft 100 in the direction of arrow C, tightening the grip of gripping members 11 on shaft 100 and allowing rotation of shaft 100;

b) rotation of the housing 2 and shaft 100 in the direction on opposite to arrow C, loosening the grip of gripping members 11 on shaft 100; and c) rotation of the housing 2 in the direction of arrow C, re-tightening the grip of gripping members 11 on shaft 100 and allowing further rotation of shaft 100.

Each cylindrical gripping member 11 or 12 may be made of a material which is harder than the cylindrical shaft. In some embodiments, the cylindrical gripping members 11 or 12 may be made from a hard ceramic material, such as silicon nitride, yttria-stabilized zirconium oxide, tungsten carbide, or silicon carbide. In some embodiments, gripping members may be made from metal, such as various steels, including iron-nickel based steel alloys and iron-chromium-manganese steel alloys and nickel-chromium based Inconel alloys. The cylindrical shaft 100 may be made from metal, e.g., titanium or stainless steel, which is softer than the material in the gripping members, thereby allowing the gripping members to slightly compress the cylindrical shaft 100. For example, stainless steel gripping members may be used to compress a shaft 100, e.g., a surgical pin, made from the softer metal titanium. Also, Type 440 stainless steel gripping members (Brinell Hardness: 269) may be used to compress a shaft 100 made from type 316 surgical grade stainless steel (Brinell Hardness: 217).

Figure 7:
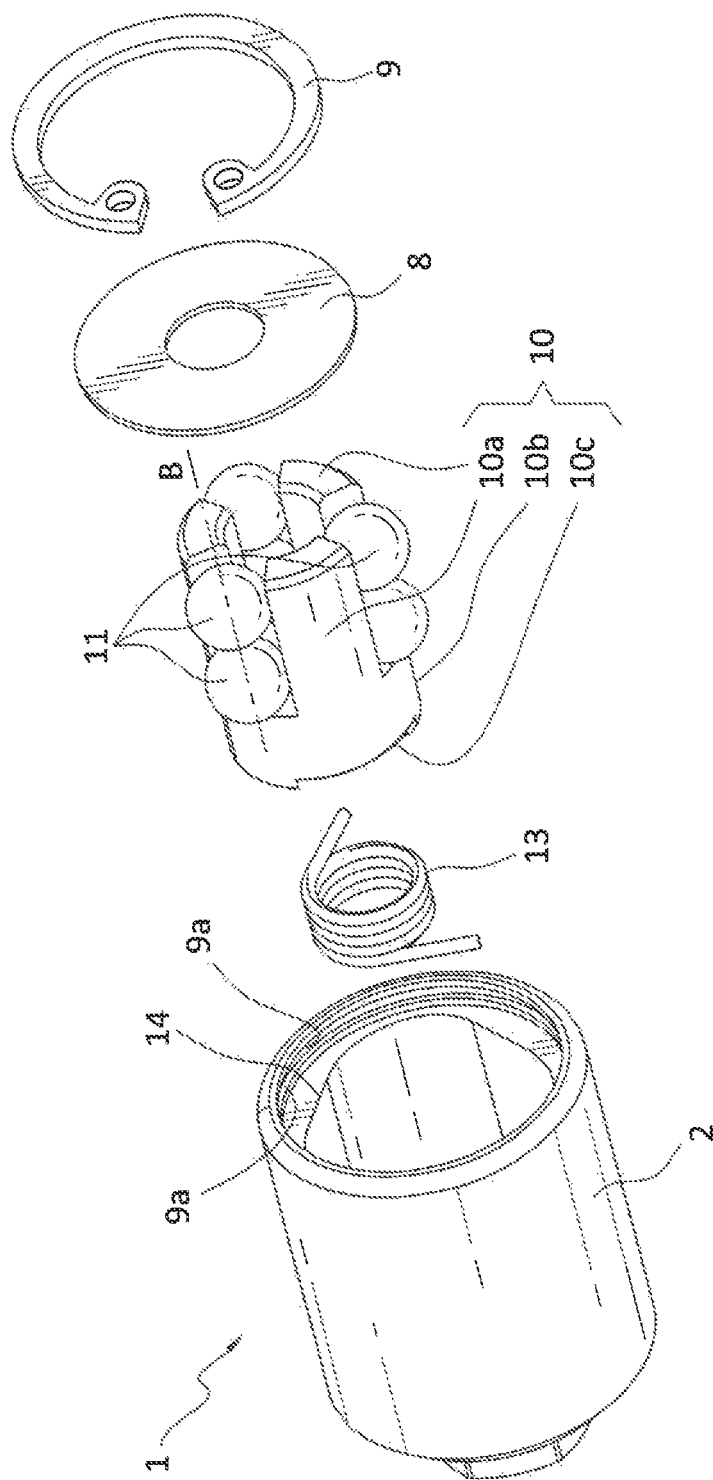
FIG. 7 illustrates an exploded view of an alternate embodiment of an apparatus for gripping a cylindrical shaft.

FIG. 7 shows an exploded view of an alternative embodiment of the apparatus 1 of FIG. 2. The apparatus of FIG. 7 includes a housing 2 with an inner cam surface 14. The apparatus of FIG. 7 also includes a spacer with a ring-shaped member 10b and a plurality of spacer arms 10a. Washer 9 fits against the upper ends of spacer arms 10a. A torsion spring 13 is placed in ring-shaped member 10b of spacer 10, so that a free end of spring 13 occupies a notch 10c in ring shaped member 10a. The apparatus of FIG. 7 differs from the apparatus of FIG. 2 in that a gripping member including a pair of spherical members 11, each able to revolve about an axis B which is parallel to an axis of housing 1, is positioned between each pair of adjacent spacer arms 10a. In contrast, the apparatus of FIG. 2 includes gripping members including a single spherical member 11 and a cylindrical member 12. In the apparatus of FIG. 7, the spherical members 11 are constrained from lateral movement, relative to spacer 10, by the inner cam surface 14 of housing 2 and the spacer arms 10a. The spherical members 11 are constrained from longitudinal movement along the axis of housing 2 by the upper surface of ring-shaped member 10b on spacer 10 and the lower surface of washer 8. Clip 9 fits above washer 8, with the edge of clip 9 fitting into a slot 9a on the inner surface of housing 2 and holding washer 8 against the distal end of housing 2. A handle or a means for attaching a handle (not shown in FIG. 7) is secured to the proximal end of housing 2.

Figure 8:
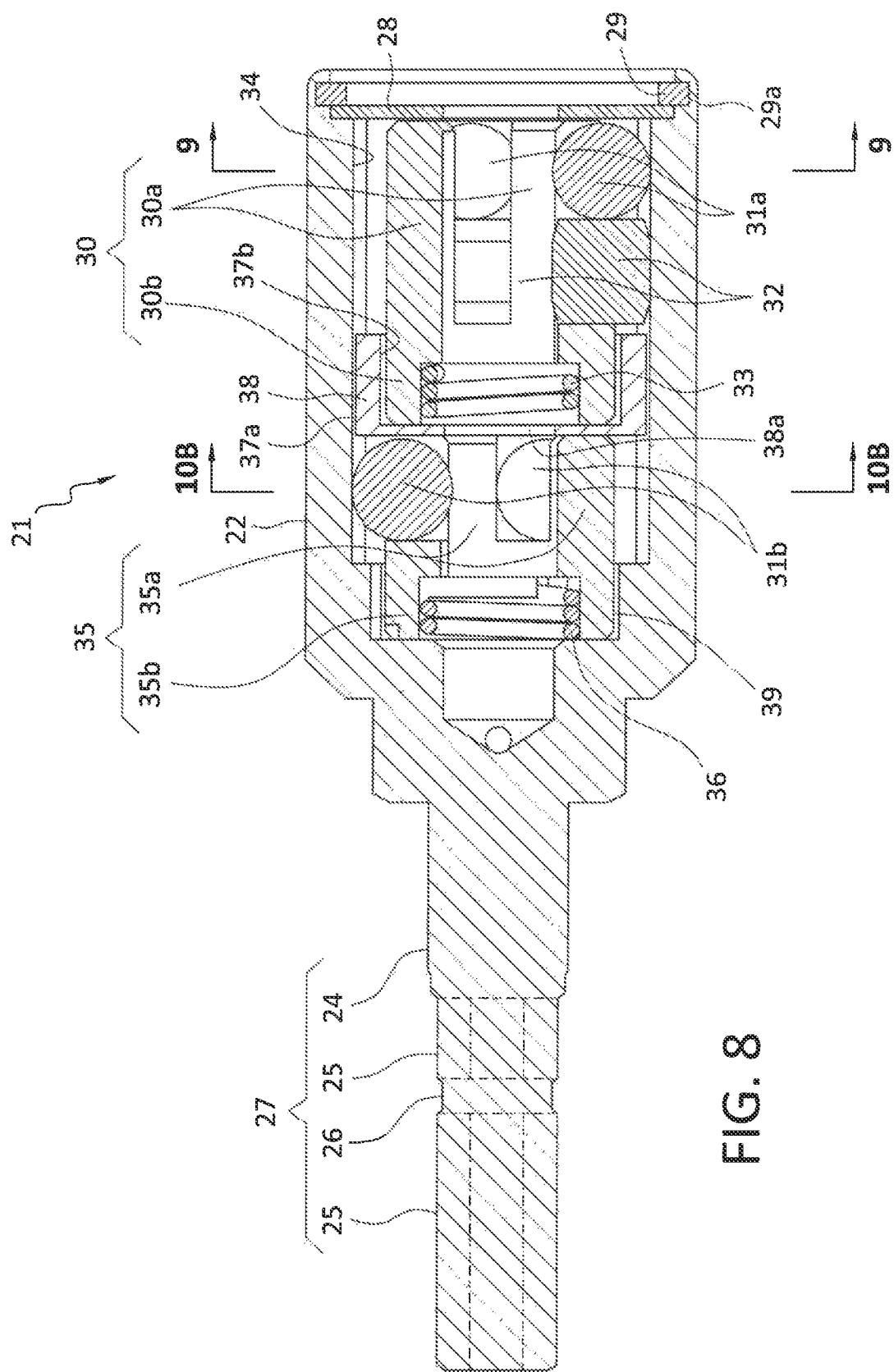
FIG. 8 illustrates a cross section view of a third embodiment of an apparatus for gripping a cylindrical shaft.
Figure 8A:
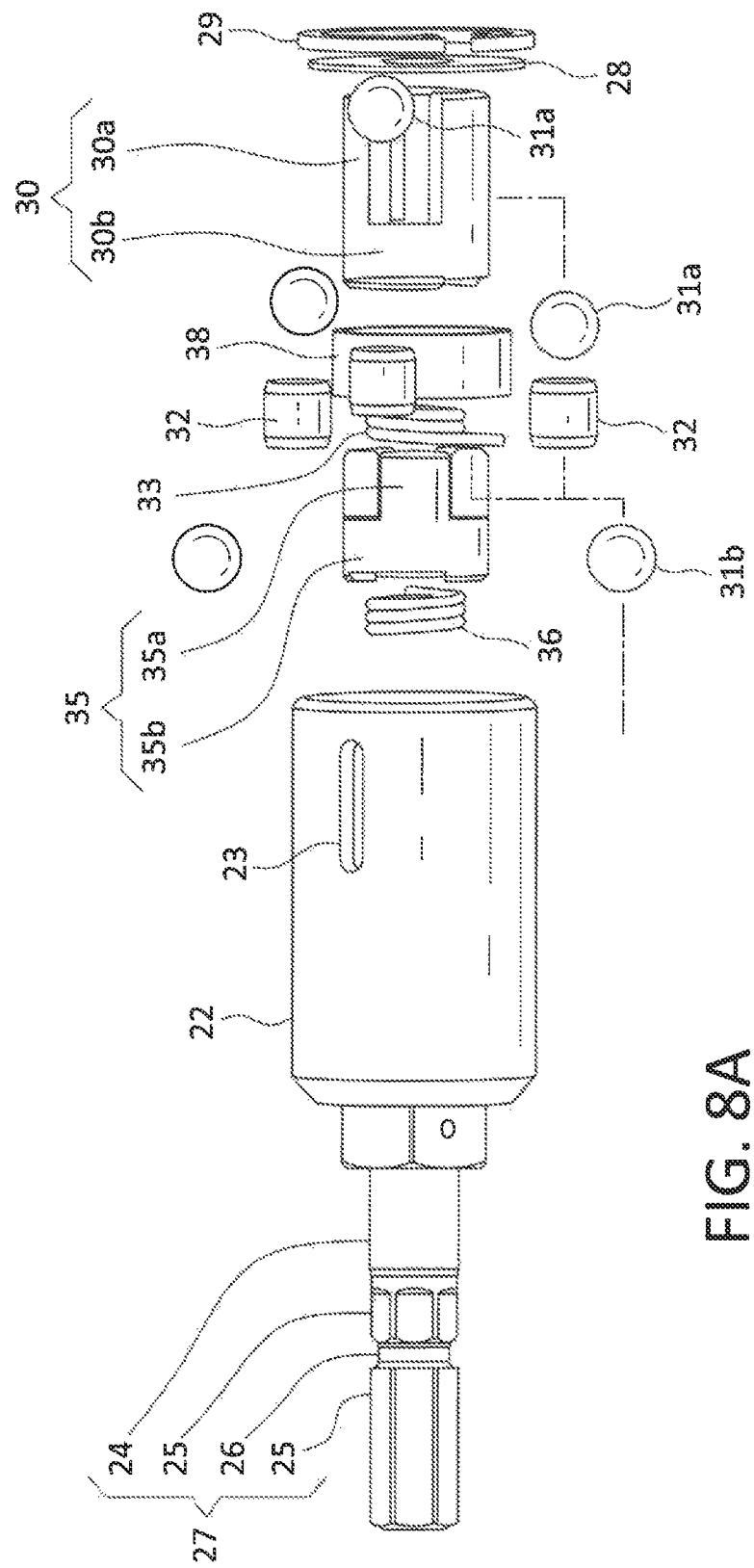
FIG. 8A illustrates an exploded view of the apparatus of FIG. 8.

FIGS. 8 and 8A show an alternative embodiment 21 of the apparatus for gripping a cylindrical shaft, e.g., a surgical pin or a drill bit. In the case of a threaded pin or a drill bit the apparatus 21 of FIG. 8 is adapted to rotate the shaft in a first direction for insertion into a desired material, e.g., bone, or in a second direction for removal of the shaft from the material. The apparatus 21 includes a cylindrical housing 22 having an inner surface 34, with a means to rotate the housing 22 at a proximal end of housing 22. In various embodiments, the means to rotate the housing 22 includes a cylindrical shaft 24 connected to a hexagonal shaft 25, where the hexagonal shaft may have a tapered end. The hexagonal shaft 25 may have a groove 26, and be configured to fit into a hexagonal bore of a handle. Retractable bearings in the handle may engage the groove 26 on hexagonal shaft 25, preventing shaft 25 from withdrawing from the handle.

The housing 22 has a cylindrical shell with optional windows 23 therethrough, where windows 23 are shown in FIG. 8A. In FIG. 8, the distal end of housing 22 includes a washer 28 held in place by a clip 29, where clip 29 fits into a notch 29a in housing 22.

The interior of housing 22 is divided into two chambers by a cup-shaped separator 38, which has an outer surface 37a which conforms to the inner surface 34 of the housing 22 and a cylindrical inner surface 37b. An opening 38a in the center of separator 38 is configured to receive the cylindrical shaft. A first spacer 30 within housing 22 has a ring-shaped member 30b which rotatably fits into inner surface 37b of separator 38. A plurality of spacer arms 30a extend from ring-shaped member 30b in a distal direction, toward washer 28. A cylindrical gripping member, a spherical gripping member, or a combination thereof is positioned between each pair of adjacent spacer arms 30a. In FIG. 8, each cylindrical gripping member includes a first spherical member 31a between two arms 30a near washer 28, and a second cylindrical member 32 adjacent to spacer ring 30b.

A second spacer 35 within housing 22 has a ring-shaped member 35b which rotatably fits into a cylindrical opening 39 at a proximal end of the interior of housing 22. A plurality of spacer arms 35a extend from ring-shaped member 35b in a distal direction, toward separator 38. A cylindrical or spherical gripping member is positioned between each pair of adjacent spacer arms 35a. In FIG. 8, each cylindrical gripping member includes a spherical member 31b between each pair of adjacent arms 35a near separator 38. If desired, the cylindrical gripping members between arms 35a may be cylindrical members or a combination of cylindrical and spherical members.

As shown in FIG. 8, a first torsion spring 33 is positioned between ring-shaped member 30b and separator 38, so that rotation of the ring-shaped member 30b in a first direction applies tension to torsion spring 33. A second torsion spring 36 is positioned between ring-shaped member 35b and cylindrical opening 39. Torsion springs 33 and 36 are coiled in opposite directions, so that rotation of the ring-shaped member 35b in a second direction which is opposite to the first direction applies tension to torsion spring 36.

FIG. 8A is an exploded view of the apparatus of FIG. 8. As seen in FIG. 8A, a first spherical gripping member 31a and a cylindrical gripping member 32 may fit into an opening between two spacer arms 30a. The inner surface of housing 22 constrains gripping members 31a and 32 from movement in a radial direction, relative to an axis of housing 2. The upper surface of ring 30b and the inner surface of washer 28 constrain gripping members 31a and 32 from movement in an axial direction.

In FIG. 8A, second spherical gripping members 31b may fit into openings between two spacer arms 35a. The inner surface of housing 22 constrains gripping members 31b from movement in a radial direction, while the upper surface of ring 35b and the lower surface of separator 38 constrain gripping members 31a and 32 from movement in an axial direction.

Figure 8B:
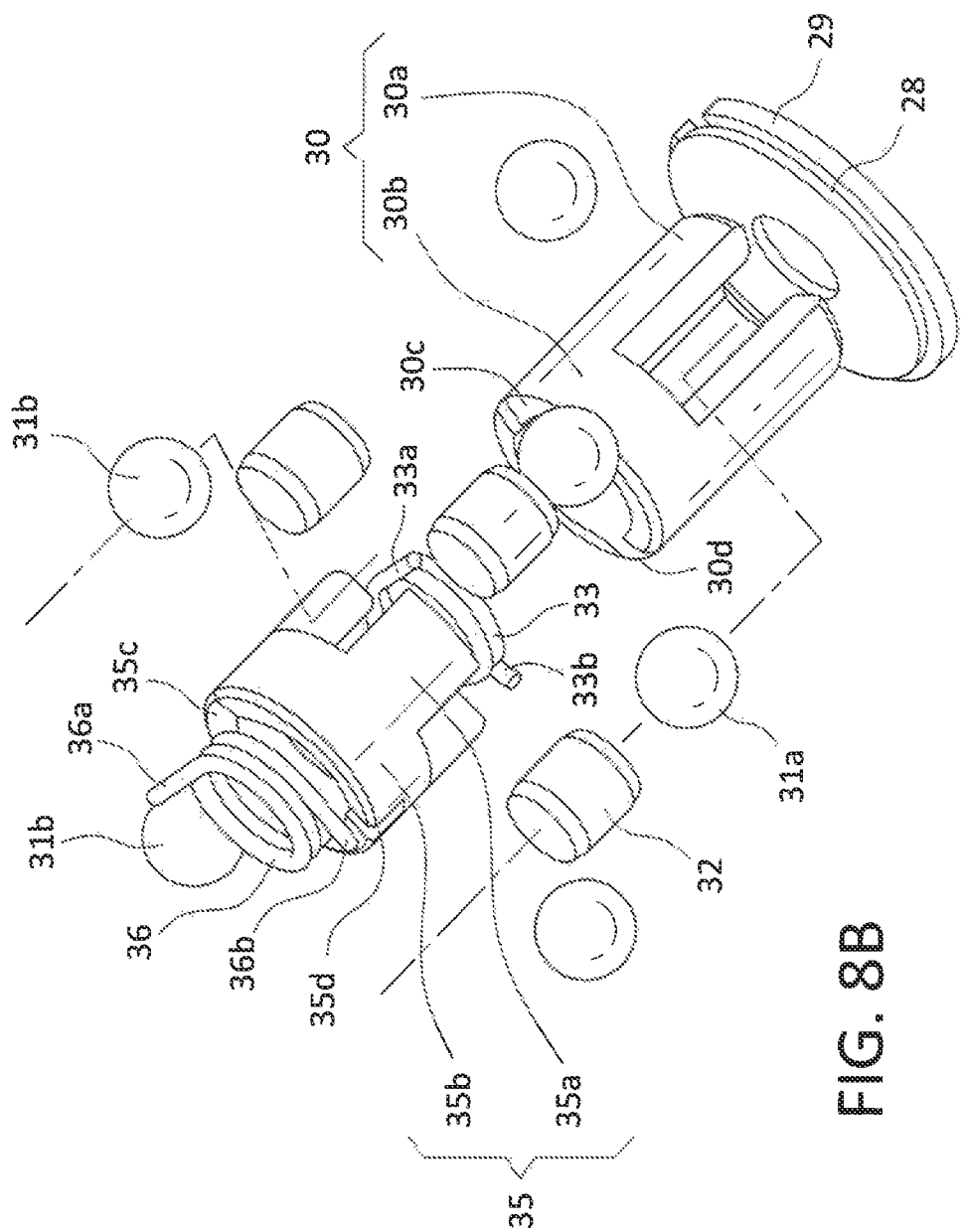
FIG. 8B illustrates an exploded view of the interior parts of the apparatus of FIG. 8.

FIG. 8B shows an exploded view of the apparatus of FIG. 8, where housing 22 and separator 38 are not shown. As seen in FIG. 8B, a first spherical gripping member 31a and a cylindrical gripping member 32 may fit into an opening between two spacer arms 30a, and a second spherical gripping members 31b may fit into openings between two spacer arms 35a. Ring 30b of spacer 30 includes a first notch 30c configured to receive an end 33a of torsion spring 33, where notch 30c allows rotation of spring end 33a in a first direction, applying tension to torsion spring 33. Ring 30b of spacer 30 also includes a second slot 30d configured to receive an end 33b of spring 33, where slot 30d prevents rotation of spring end 33b, preventing the release of tension generated by rotation of spring end 33a.

Also, FIG. 8B shows ring 35b of spacer 35 includes a first notch 35c configured to receive an end 36a of torsion spring 36, where notch 36c allows rotation of spring end 36a in a second direction, applying tension to torsion spring 36. Ring 35b of spacer 35 also includes a second slot 35d configured to receive an end 36b of spring 36, where slot 35d prevents rotation of spring end 36b, preventing the release of tension generated by rotation of spring end 36a. As seen in FIG. 8B, springs 33 and 36 are coiled in opposite directions, so that: rotation of spring end 33a in the first direction applies tension to spring 33, while rotation of spring end 36a in the second direction applies tension to spring 36, where the second direction is opposite to the first direction.

In various embodiments, each gripping member may be formed of a single cylindrical member 32. Alternatively, each gripping member may be formed of two or more spherical members 31. The gripping members are retained in position by arms 30a on each side and washer 28 at the distal end of the housing 22. Washer 28 is retained in position by clip 29, which fits into a circumferential slot on an inner surface of housing 22. The gripping members define a space which is configured to receive a cylindrical shaft 100 as shown in FIG. 2, which may be inserted through the opening in washer 28.

Figure 9:
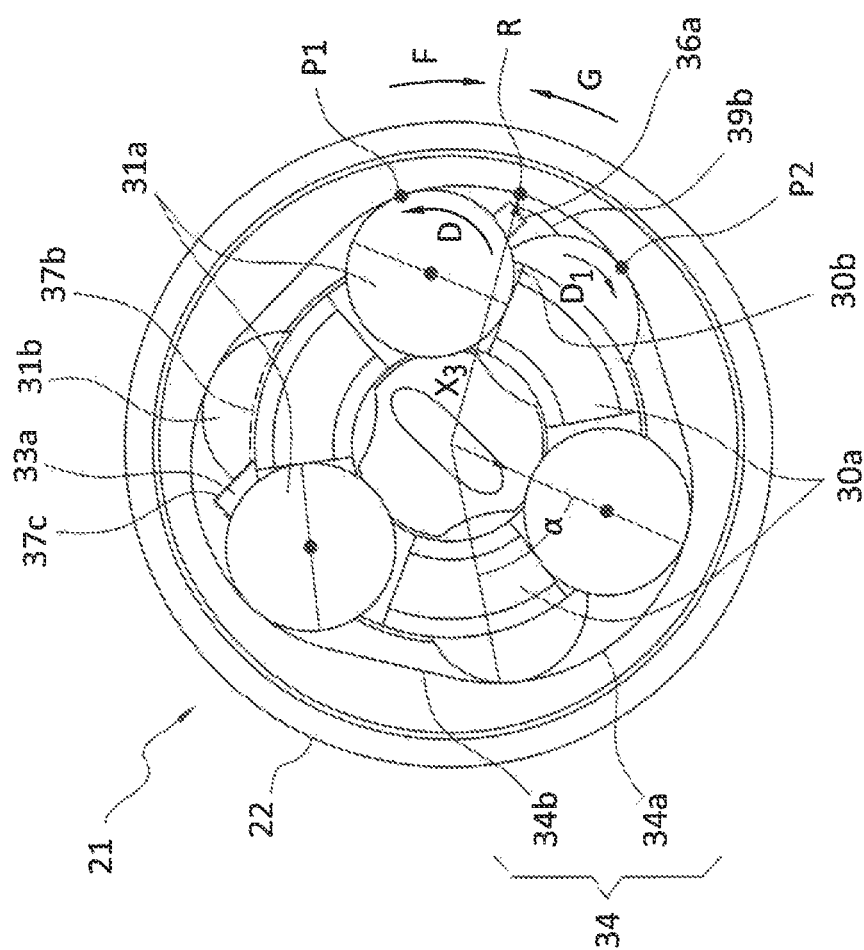
FIG. 9 shows a cross section view of the apparatus of FIG. 8, in the plane holding arrows 9 in FIG. 8, where separator 38 is not shown.

FIG. 9 is a view of the apparatus of FIG. 8, in a plane occupied by arrows 9 in FIG. 8. For purposes of clarity, separator 38 is not shown, although a portion of the interior surface 37b of separator 38 is shown with a broken line. In FIG. 9, the inner surface 34 of housing 22 includes a plurality of symmetric or slightly asymmetric curved camming surfaces 34a, joined by generally planar surfaces 34b. Spacer 30 is positioned so that spacer arms 30a hold each gripping member 31a (gripping members 32, below members 31a, are not shown in FIG. 9) against a first edge of a curved camming surface 34a at point P1. Spacer 35 (shown in FIG. 9) is positioned so that spacer arms 35a hold each gripping member 31b against a second edge of camming surface 34a at point P2, opposite to the first edge of camming surface 34a. Each pair of upper gripping members 31a are offset from a lower gripping member 31b by an angle α.

Gripping members 31a and 31b collectively define a space adapted to receive a cylindrical shaft; however, when upper and lower gripping members 31a and 31b are offset by angle α, this space is smaller than the diameter of the shaft. As the cylindrical shaft passes spherical gripping members 31a, members 31a rotate in the direction of arrow D, allowing members 31a to roll along cam surface 34a in the direction of arrow F from point P1 toward point R. When members 31a reach point R, members 31a are spaced sufficiently far apart to allow the cylindrical shaft to pass therebetween. At this point, the housing may be further rotated in the direction of arrow F, causing the gripping members 31a to rotate along cam surface 34a in a direction opposite to arrow F, tightening the grip of gripping members 31a on shaft 100. Where shaft 100 is a Schanz pin, further rotation of the housing in direction F results in unscrewing the pin. Rotation of housing 22 in a direction opposite to arrow F loosens the grip of the gripping members 31a on the shaft 100, allowing shaft 100 to be removed from housing 22.

After the cylindrical shaft passes spherical gripping members 31a, the shaft contacts members 31b. As the shaft passes members 31b, members 31b rotate in the direction of arrow D1, allowing members 31b to roll along cam surface 34a in the direction of arrow G from point P2 toward point R. When members 31b reach point R, members 31b are spaced sufficiently far apart to allow the cylindrical shaft to pass therebetween. At this point, the housing 22 may be further rotated in the direction of arrow G, causing gripping members 31b to rotate along cam surface 34a toward point P2, in a direction opposite to arrow G. This causes members 31b to grip the cylindrical shaft and allows rotation of the shaft in direction G. Thus, the apparatus of FIG. 8 allows for rotation of a cylindrical shaft in either of two opposite directions with a single tool, and may thus be used for either insertion or removal of a threaded shaft, e.g., a Schanz pin or drill bit.

The above discussion suggests that, upon insertion of shaft 100, members 31a and 31b each contact point R on cam surface 34a, so that an offset angle α between upper and lower gripping members 31a and 31b is zero, i.e., members 31a and 31b are essentially coaxial. This is dependent on the sum of the diameter of gripping members 31a and 31b and the radius of shaft 100 being equal to a distance between an axis of housing 22 and the inner surface of housing 22 at point R ($x_3$ in FIG. 9). The sum of the diameter of the gripping members and the radius of shaft 100 may be less than $x_3$ but greater than a distance between an axis of housing 22 and the inner surface of housing 22 at their initial position P1 or P2. In such cases, upon insertion of shaft 100, members 31a and 31b may come to rest on cam surface 34a at a point between their initial position and point R, with a nonzero offset angle.

As mentioned above, a portion of the interior surface 37b of separator 38 in is shown with a broken line in the apparatus of FIG. 9. The free end 33a of spring 33 is pressed against a surface of a notch 37c in the cylindrical opening 37b in separator 38. Rotation of spacer 30 relative to housing 22 is prevented prior to insertion of a cylindrical shaft by contact between the wall of notch 37c and spring end 33a. This biases spacer 30 into a position where gripping members 31a each rest against an inner surface of housing 22 at a point P1. As shaft 100, as shown in FIG. 2, is inserted and spacer 30 rotates in the direction of arrow F, the tension on torsion spring 33 increases, with the free end 33a of torsion spring moving out of notch 37c as the spacer 30 rotates.

Also as shown in FIG. 9, the free end 36a of spring 36 is pressed against a surface of a lobe 39b in cylindrical opening 39, occupied by the second spacer 35 (shown in FIG. 8). Rotation of spacer 35, and gripping members 31b carried by spacer 35, relative to housing 22 is prevented by contact between spring end 36a and the wall of lobe 39b. Spacer 35 is biased into a position where gripping members 31b each rest against an inner surface of housing 22 at a point P2. As shaft 100 is inserted past gripping members 31b, spacer 35 rotates in the direction of arrow G. Rotation of spacer 35 causes the tension on torsion spring 36 to increase, with the free end 36a of torsion spring 36 moving out of lobe 39b as the spacer 35 rotates. As seen in FIG. 8, torsion springs 33 and 36 are wound in opposite directions. As seen in FIG. 9, torsion springs 33 and 36 cause the spacers 30 and 35 to rotate in opposite directions as the cylindrical shaft moves axially past 31a and 31b.

Figure 10A:
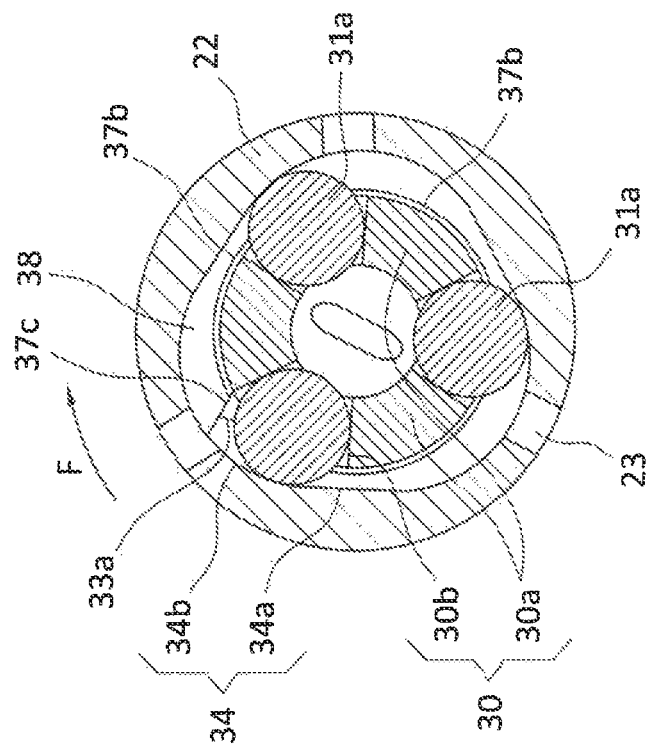
FIG. 10A shows a cross section view of the apparatus of FIG. 8, in the plane holding arrows 9 in FIG. 8, where separator 38 is shown.

FIG. 10A shows another view of the apparatus of FIG. 8, in a plane occupied by arrows 9 in FIG. 8, where separator 30 is shown. The outer edge of the separator 38 conforms to the inner surface 34 of housing 22. A cylindrical opening 37 rotatably receives spacer 30. A torsion spring 33, shown in FIG. 8, is positioned within spacer 30. The torsion spring 33 has a free end 33a, which is received in a notch 37a in separator 38 and biases the spacer into an orientation where gripping members 31a are each held against a first position at a first edge of cam surface 34 in housing 22. As the cylindrical member is pushed past gripping members 31a, members 31a rotate along cam surfaces 34a in the direction of arrow F, allowing members 31a to move away from an axis of housing 22 and grip the cylindrical shaft. As members 31a rotate, spring end 33a moves out of notch 37a, applying tension to spring 33.

Figure 10B:
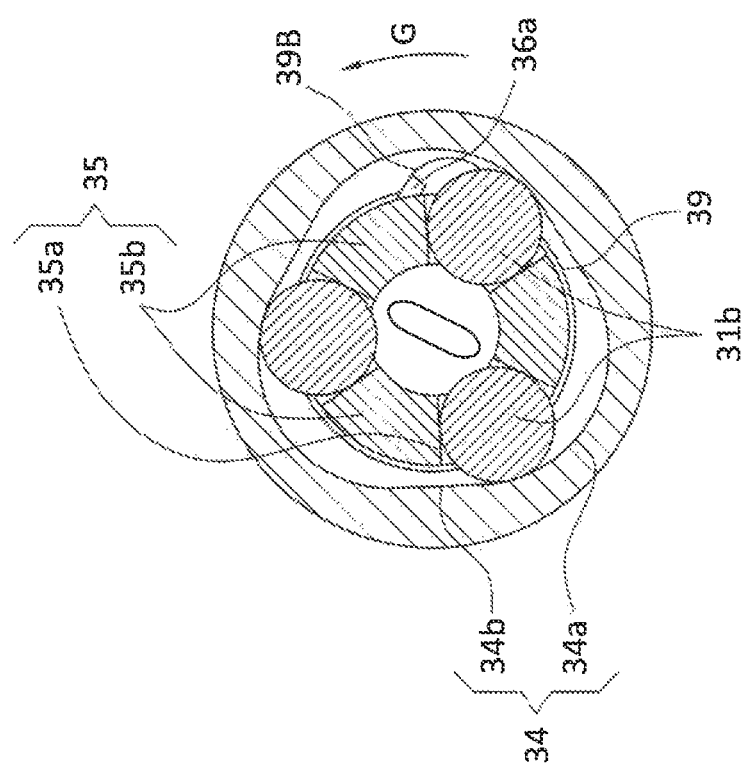
FIG. 10B shows a cross section view of the apparatus of FIG. 8, in the plane holding arrows 10B in FIG. 8.

FIG. 10B shows a view of the apparatus of FIG. 8, in a plane occupied by arrows 10B in FIG. 8. A cylindrical opening 39 at the distal end of the housing 22 rotatably receives spacer 35. A torsion spring 36, shown in FIG. 8, is positioned within spacer 35. The torsion spring 36 has a free end 36a, which is received in a lobe 39b in cylindrical opening 39 and biases the spacer 35 into an orientation where gripping members 31b are each held against a second position at a second edge of cam surface 34 in housing 22, where the first and second edges of cam surface 34 are opposite each other. As the cylindrical member is pushed past gripping members 31b, members 31b rotate along cam surfaces 34a in the direction of arrow G, allowing members 31a to move away from an axis of housing 22 and grip the cylindrical shaft. As members 31a rotate, spring end 36a moves out of lobe 39b, applying tension to spring 35.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. An apparatus for gripping a cylindrical shaft, comprising:
   a housing having an axis and an inner surface with multiple asymmetric cam surfaces, a proximal end comprising a means to rotate the housing, and a distal end having an opening configured to receive the cylindrical shaft,
   at least two gripping members configured to apply a deforming force to the cylindrical shaft, where each gripping member comprises:
      a spherical gripping member contacting a corresponding one of the asymmetric cam surfaces at a first rest position, and
      a second gripping member, the second gripping member being coaxial with the spherical gripping member; and
   a rotatable frame which holds each pair of the gripping members at a fixed angular orientation relative to each other,
   wherein:
      the rotatable frame is biased into a first position relative to the housing where each said spherical gripping member and each said second gripping member contact a first portion of the corresponding one of the asymmetric cam surfaces at the first rest position;
      the rotatable frame is configured to rotate in a first direction relative to the housing upon insertion of the cylindrical shaft into a space defined by the spherical gripping members so that each said gripping member moves away from the axis of the housing along the first portion of the corresponding one of the asymmetric cam surfaces; and
      after insertion of the cylindrical shaft, the rotatable frame is configured to rotate in a second direction relative to the housing so as to cause each said spherical gripping member to apply the deforming force by moving toward the axis of the housing along a second portion of the corresponding one of the asymmetric cam surfaces.

2. The apparatus of claim 1, wherein the rotatable frame is biased into the first position by a torsion spring within the rotatable frame, wherein the torsion spring engages the housing; and
   rotation of the rotatable frame relative to the housing disengages the torsion spring from the housing.

3. The apparatus of claim 1, wherein each said coaxial second gripping member is independently selected from the group consisting of a spherical gripping member, a right cylindrical gripping member having planar ends, and a cylindrical gripping member having non-planar ends.

4. The apparatus of claim 3, wherein each said second gripping members is a cylindrical gripping member.

5. The apparatus of claim 4, wherein each said second gripping member is a cylindrical gripping member having non-planar ends.

6. The apparatus of claim 5, wherein each said second gripping member is a cylindrical gripping member having frustoconical ends, dome shaped ends, or a combination thereof.

7. The apparatus of claim 1, wherein each said spherical gripping member is made of a material which is harder than the cylindrical shaft, where the material is selected from the group consisting of silicon nitride, zirconium oxide, silicon carbide, and stainless steel.

8. The apparatus of claim 1, wherein:
   each pair of adjacent ones of the asymmetric cam surfaces is connected by a substantially planar surface,
   the first portion of each of the asymmetric cam surfaces has a first curvature, and
   the second portion of each of the asymmetric cam surfaces has a second curvature which is greater than the first curvature.

9. The apparatus of claim 1, wherein the means to rotate the housing comprises a handle.

10. The apparatus of claim 1, wherein the means to rotate the housing comprises a shaft having a first planar surface, the shaft being configured to engage a handle with a bore having a corresponding second planar surface, the shaft having a groove therein, the groove being configured to engage a ball bearing mounted in the bore.

11. The apparatus of claim 1, wherein the means to rotate the housing comprises a hexagonal shaft configured to engage a handle with a hexagonal bore, the hexagonal shaft having a groove therein, the groove being configured to engage a ball bearing mounted in the hexagonal bore.

12. A method for removing a cylindrical shaft from a material using the apparatus of claim 1, comprising:
   inserting the cylindrical shaft into the opening at the distal end of the housing when each said spherical gripping member contacts the first portion of the corresponding one of the asymmetric cam surfaces at the first rest position;
   pushing the cylindrical shaft into the space defined by the spherical gripping members so as to cause each said spherical gripping member to move away from the axis of the housing along the first portion of the corresponding one of the asymmetric cam surfaces, thereby expanding the space defined by the spherical gripping members until it accepts the cylindrical shaft;

after insertion of the cylindrical shaft, rotating the housing relative to the rotatable frame so as to cause each gripping member to move toward the axis of the housing along the second portion of the corresponding one of the asymmetric cam surfaces until the cylindrical shaft is gripped and deformed by the spherical gripping members; and removing the deformed shaft from the from the material.

13. The method of claim 12, wherein the cylindrical shaft is a surgical pin, and the material is bone.

* * * * *